United States Patent [19]

Dallas

[11] Patent Number: 5,489,744
[45] Date of Patent: Feb. 6, 1996

[54] INBRED CORN LINE 4P33339

[75] Inventor: Lyndall W. Dallas, Lincoln, Ill.

[73] Assignee: Agrigenetrics, L.P., Madison, Wis.

[21] Appl. No.: 95,286

[22] Filed: Jul. 21, 1993

[51] Int. Cl.$^6$ ............................... A01H 1/02; A01H 4/00; A01H 5/00; C12N 5/04

[52] U.S. Cl. .................. 800/200; 800/250; 800/DIG. 56; 435/240.4; 435/240.49; 435/240.5; 47/58; 47/DIG. 1

[58] Field of Search ...................................... 800/200, 250, 800/DIG. 52, DIG. 56, 205, 235; 435/172.1, 172.3, 240.4, 240.1, 240.47, 240.49, 240.5; 47/58.03, 58.01

[56] References Cited

U.S. PATENT DOCUMENTS 5,059,745   10/1991   Foley ........................................ 800/200

OTHER PUBLICATIONS

Hallauer et al. 1988 In: Corn and Corn Improvement Sprague et al., eds. Ch 8:463–564.
Phillips et al. 1988 In: Corn and Corn Improvement Sprague et al., eds. Ch 5:345–387.
Bradley et al. 1988 J. Prod. Agric. 1(1):34–38.
Hallauer et al. 1982 Quantitative Genetics in Maize Breeding pp. 123–126.
Meghji et al. 1984. Crop Science 545–549.
Allard. 1960, Plant Breeding pp. 68–69.
Edallo et al. 1981. Maydica. 26:39–56.

Primary Examiner—Gary Benzion
Assistant Examiner—Erich E. Veitenheimer
Attorney, Agent, or Firm—Saliwanchik & Saliwanchik

[57] ABSTRACT

According to the invention, there is provided an inbred corn line, designated 4P33339. Further provided are the plants and seeds of inbred corn line 4P33339, and hybrids produced using 4P33339 inbred line as one parent crossed with a distinct inbred corn line.

7 Claims, No Drawings

INBRED CORN LINE 4P33339

FIELD OF THE INVENTION

This invention relates to the field of corn breeding, and, more particularly, relates to an inbred corn line useful for creating high quality hybrid corn.

BACKGROUND OF THE INVENTION

The commercial value of field corn as a source of food and other products owes in large part to the development of hybrid seed. Virtually all corn grown commercially in the United States is planted from hybrid seed. Hybrid corn is generally understood to be the first generation of a cross between inbred lines, which have been developed by controlled self-pollination continued for several generations.

Inbred corn lines have genetically pure or homozygous genotypes. They will generally have desirable agronomic characteristics and be relatively resistant to insect and disease attacks, but will usually display reduced vigor and yield. Provided that the inbred parent lines are not closely related, corn hybrids will generally exhibit heterosis or hybrid vigor, i.e., which includes, yield greater than expected from either parent inbred line.

Typically, a commercially valuable inbred corn line results from plants that have been self-pollinated and selected for type for many generations. The plants become homozygous at almost all gene loci. Meiosis yields gametes of uniform genotype, and they produce a uniform population of true breeding progeny. A cross between two homozygous, inbred parent lines, each line producing uniform gametes, produces a uniform population of hybrid plants that may be heterozygous for many gene loci.

The development of high yielding corn hybrids that are agronomically sound based on stable inbred lines involves three steps: (1) the selection of plants from various germplasm pools; (2) the selfing of the selected plants for several generations to produce a series of parent inbred lines, each, although distinct from the others, breeding true and highly uniform, ; and (3) crossing the selected parent inbred lines with unrelated parent inbred lines to produce the hybrid progeny ($F_1$).

During the inbreeding process in corn, the vigor of the line decreases. Vigor is restored when two unrelated inbred lines are crossed to produce the hybrid progeny (F1). An important consequence of the homozygosity and homogeneity of the parent inbred lines is that the hybrid between any two parent inbred lines will always be substantially the same. Once the parent inbred lines that give a superior hybrid have been identified, the hybrid seed can be reproduced indefinitely as long as the homogeneity of the inbred parent lines is maintained.

The breeder develops superior, inbred parental lines for producing hybrids by identifying and selecting in the progeny of diverse parents rare individuals having a desired phenotype or combination of traits based on a unique genetic endowment, which the breeder attempts to preserve by controlled inbreeding.

SUMMARY OF THE INVENTION

The present invention provides a novel inbred *Zea mays* L. corn line, designated 4P33339, adapted for a wide general combining ability. Also provided in the present invention are seeds of inbred corn line 4P33339 and the plants produced from seeds of inbred corn line 4P33339. The invention further provides for hybrid corn plants produced from a cross between 4P33339 and a distinct second inbred *Zea mays* L. corn line. Also provided are tissue cultures of regenerable cells of the corn plant grown from 4P33339 seed as well as tissue cultures of regenerable cells of the hybrid corn plants produced from a cross between 4P33339 and a distinct second inbred *Zea mays* L. corn line.

Definitions

As used herein, the following definitions are provided:

Apr—Appearance rating, which is a visual rating scaled from 1–5 of plant appearance on a plot basis; the lower the rating, the better the plant appearance. Appearance rating is equivalent to stay green, which is a measure of plant health at harvest.

Drop ear—refers to dropped ears, which is a measure of the number of dropped ears per plot, and represents the percentage of plants for which ears were lost prior to harvest.

Ear ht—refers to ear height, which is a measure from the ground to the top developed ear node attachment in inches.

Emr—refers to emergence rating, which is a visual rating scaled from 1–5 of seedling vigor on a plot basis; the lower the rating, the better the seedling vigor.

Kernel % >18.5—refers to the percentage of harvested grain that is larger than an 18 ½ round screen.

Kernel % 18.5–16.5—refers to the percentage of harvested grain that is smaller than an 18 ½ round screen, but larger than a 16 ½ round screen.

Kernel % <16.5—refers to the percentage of harvested grain that is smaller than a 16 ½ round screen; this portion of harvested seed is usually discarded as too small for planting.

Pop—refers to population tested. The number given is the number in thousands of plants when converted to an acre basis.

Pt Ht—refers to plant height, which is a measure of the height of the plant from the ground to the tip of the tassel in inches.

Root Lodg—refers to root lodging, which is the percentage of plants that root lodge, i.e., plants that lean from the vertical axis at an approximately 30° angle or greater would be counted as root lodged.

Stlk Lodg—refers to stalk lodging, which is the percentage of plants that stalk lodge (stalk breakage) as measured by natural lodging of the stalks. It is determined by counting the number of plants that have broken over below the ear.

Tst Wt—refers to test weight, which is the pound of grain contained in a unit volume (bushel).

YLD—refers to yield, which is the bushels of grain harvested per acre, converted to 15.5% moisture.

Y/M—refers to yield/percent moisture; the higher this index, the more commercially valuable is the corn.

% MST—refers to percent moisture, which is the actual moisture of the grain at harvest.

Susc.—means susceptible.

Res.—means resistant.

Selection—occurs when plants with desired phenotypes or genotypes are chosen for additional plant breeding procedures and breeding projects.

Variety—a term used interchangeably with "cultivar" to denote a group of plants within a species, such as *Zea mays* L., which share certain stable characteristics that separate them from other possible varieties within that species. While possessing at least one distinctive trait, a variety can also be characterized by a substantial amount of variation between individuals within the variety, based primarily on the Mendelian segregation of traits among the progeny of succeeding generations.

Line—a line, as distinguished from "variety" and "cultivar," refers to a group of plants which are substantially uniform in their traits such that there is relatively minor variation within the group and such variation can be characterized. The decreased variation within this group has generally (although not exclusively) resulted from several generations of self pollination (selfing).

Heritable—a trait in a line or variety is considered heritable where the trait is genetically determined to the extent that when the line is crossed with a distinct line, the trait is passed on to the progeny. The trait is therefore considered heritable as it can be conferred upon hybrids which have the line as one of their parental antecedents.

True Breeding—a line or variety is considered true breeding for a particular trait where it is genetically homozygous for that trait to the extent that when the line is self-pollinated, no significant amount of independent segregation of the trait among progeny is observed. The trait is therefore considered "fixed." This may also be defined in terms of whether the progeny shown any significant variation with regard to the particular trait; if there is no significant variation, then the line is true breeding.

Commercially Acceptable Variety—any variety, including inbreds and hybrids, which yields plants having agronomically acceptable traits. Such traits may relate to desirable factors such as high yield, a fast rate of dry-down, low stalk lodging, low root lodging, disease resistance, insect resistance, and the like, such that a) with respect to inbreds, these traits allow the economical use of this genotype in the production of hybrid seed, or b) with respect to hybrids, the acceptable traits are present in the hybrid plants when grown in a farmer's field.

DETAILED DESCRIPTION OF THE INVENTION

Inbred *Zea mays* L. corn line 4P33339 is a yellow, dent corn inbred with superior characteristics and provides an excellent female parental inbred line yielding gametes of uniform genotype for crossing preferably with a variety or cultivar of *Zea mays* L. to produce first generation $F_1$ corn hybrids. The 4P33339 inbred line is best adapted over the Northern and Central regions of the United States and Southern Canada (Ontario). The 4P33339 parent inbred line can be used to produce commercially acceptable varieties of hybrids from approximately 95–110 relative maturity based on the Minnesota Relative Maturity Rating System for harvesting moisture of grain. Because of its excellent yielding ability and good sizing, the 4P33339 parent inbred line is best used as a female parent.

The 4P33339 inbred line has shown uniformity and stability within the limits of environmental influence for all the traits as described in the Variety Description Information (Table 1) that follows. Such uniformity and stability demonstrates that the 4P33339 parent inbred line produces gametes of uniform genotype. Table 1 compares the traits of corn plants grown from 4P33339 inbred line seed to those for inbred corn line B73, a publicly available inbred line (released from Iowa State University) which served as one parent in the development of the parent inbred line 4P33339. Most of the data in Table 1 was collected at Lincoln, Ill.

The genotype of the claimed 4P33339 parent inbred line is additionally characterized by its isozyme content as shown in Table 2, and by its yield and kernel characteristics in Table 3.

The inbred line 4P33339 has been self-pollinated and ear-rowed for a sufficient number of generations with careful attention paid to selecting uniformity of plant type to ensure homozygosity and phenotypic stability. The homozygosity and phenotypic stability of the 4P33339 inbred line are maintained by the claimed inbred line's production of gametes having a uniform genotype. The claimed 4P33339 inbred line has been increased both by hand and in isolated fields with continued observation for uniformity. No variant traits have been observed or are expected in the 4P33339 inbred line.

Inbred corn line 4P33339, being substantially homozygous, can be reproduced by planting seeds of the 4P33339 inbred line, growing the resulting corn plants under self-pollinating or sib-pollinating conditions with adequate isolation, and harvesting the resulting seed using techniques familiar to the agricultural arts.

Industrial Applicability

The present invention provides hybrid corn plants produced from a cross between the 4P33339 parent inbred line and a second inbred *Zea mays* L. corn line sufficiently unrelated so that a hybrid created between the two inbred lines will exhibit heterosis, i.e., increased vigor and yield. All plants produced using parent inbred corn line 4P33339 as a parent in crosses with a cultivar of *Zea mays* L. are within the scope of this invention. The 4P33339 parent inbred line is used in crosses with other distinct parent *Zea mays* L. corn inbred lines to yield $F_1$ corn hybrid seeds and plants exhibiting heterosis, i.e., superior characteristics (a commercially acceptable variety).

As used herein, the term "plants and plant parts" includes plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Regeneration of plants and plant parts from a parent inbred corn line or from a hybrid produced from a cross of two inbred corn lines is most common and in accordance with principles well known in the art. Only in the most unusual circumstances is regeneration from a line impossible. In any given line, regenerable tissue culture is available from some part of the plant making it possible to obtain regeneration of any line. While one may not be able to obtain regeneration from some parts of the corn plant, only in rare instances with present technology can one not obtain regeneration in any circumstances. Duncan et al. (*Planta* (1985) 165:322–332) discloses that 97 percent of the hybrid cultures which produce callus are capable of plant regeneration. Subsequent experiments with both inbred lines and hybrids produced 91 percent regenerable callus, which regenerated plants. Songstad et al. (*Plant cell Reports* (1988) 7:262–265) reported several media additions which enhanced regenerability of callus of two inbred lines. Other published reports also indicate that "nontraditional" tissues are capable of producing somatic embryogenesis and plant regeneration. K. V. Rao et al. (*Maize Genetics Cooperation Newsletter*(1986) 60:64–65) refers to somatic embryogenesis from glume callus cultures, and B. V. Conger et al. (*Plant Cell*

*Reports* (1987) 6:345–347) indicates somatic embryogenesis from tissue cultures of maize leaf segments. Accordingly, one of ordinary skill in the art using conventional cell and tissue culture methods as referenced above is able to routinely obtain plants or plant parts with a high rate of success from regenerable cells of a tissue culture.

Tissue culture of corn is also described in European Patent Application, publication number 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va., 1982, pp. 367–372).

Accordingly, a further aspect of this invention provides cells which upon growth and differentiation produce the inbred line 4P33339. Further provided are cells which upon growth and differentiation produce a hybrid corn plant having a genotype derived from the fusion of a gamete produced by a 4P33339 inbred line plant and gamete of the opposite sex produced by a second, inbred line of *Zea mays* L.

The seed of inbred corn line 4P33339, the plant produced from the inbred seed, the hybrid corn plant produced from the crossing of the claimed inbred, hybrid seed thereof, and various parts of the hybrid corn plant can be utilized for human food, livestock feed, and as raw material in industry.

EXAMPLES

The key characteristics and traits of the 4P33339 inbred line are presented in the data of Tables 1, 2, and 3. In Tables 1 and 3, Applicant distinguishes the claimed 4P33339 inbred from the B73 inbred line, which is a commercially available inbred which served as one parent in the development of the 4P33339 inbred line. These tables present extensive morphological and physiological differences between the 4P33339 inbred line and the B73 inbred line.

Hybrid Performance of 4P33339

Genetic differences between claimed hybrids having 4P33339 as an inbred parent and various comparison hybrids are evidenced in Table 4 which presents the characteristics of the 4P33339 inbred line for a number of traits in hybrid combination. Each hybrid genome derives from the combination of a first 4P33339 inbred line gamete and a second gamete from a second distinct *Zea mays* L. inbred line, and is referred to hereafter as a 4P33339 hybrid. The results in Table 4 also compare hybrids produced using the 4P33339 inbred line as a first parent to commercial hybrids.

In the first three comparisons, the performance of a claimed 4P33339 hybrid is compared to that of a hybrid which has one parent in common, that parent not being the 4P33339 inbred line. The last two comparisons of Table 4 compare the performance of two 4P33339 hybrids with that of a commercially available hybrid, P3733.

In the first comparison of Table 4, test hybrid no. 1 is Jacques 4770, which is commercially available and widely grown in the area where the 4P33339 hybrid is adapted. The 4P33339 hybrid has a 3% yield advantage, greater resistance to stalk lodging, root lodging and dropped ear, and is a slightly shorter plant with a slightly lower ear than Jacques 4770 (Test hybrid no. 1), which gives the 4P33339 hybrid significant advantages over the Jacques 4770 hybrid. The last two comparisons in Table 4 employ the P3733 hybrid, which is commercially available.

The results indicate significant genetic differences for hybrid production between the claimed 4P33339 inbred line and the prior art inbred lines despite adaptation to the same region and numerous phenotypic similarities. In hybrid combination, the claimed inbred line 4P33339 provided significant improvement in agronomic characteristics of yield and resistance to stalk lodging, root lodging, and dropped ear when compared to the hybrid performance of prior art inbreds crossed to identical inbred lines.

Deposits

Applicant has made available to the public without restriction a deposit of at least 2500 seeds of the 4P33339 inbred line with the American Type Culture Collection (ATCC), Rockville, Md. 20852. The deposit has been designated as ATCC Deposit No. 97177. The seeds deposited have been maintained since prior to the filing date of the present application by Agrigenetics L. P., 5649 East Buckeye Road, Madison, Wis. 53716. The deposit of the inbred corn line 4P33339 without restriction will be maintained at the ATCC Depository, which is a public depository, for a period of 30 years, or five years after the most recent request, or for the effective life of the patent, whichever is longer, and will be replaced if it becomes nonviable during that period.

TABLE 1

4P33339
VARIETY DESCRIPTION INFORMATION

| Type: | 4P33339 dent | B73 dent |
|---|---|---|
| A. SEEDING STAGE | | |
| Seedling vigor: | high | high |
| Plant ht. at 7 leaf stage (cm): | 67 | 89 |
| Anthocyanin pigment at seedling stage: | low | low |
| B. FLOWERING STAGE | | |
| Anthocyanin color at glume tip: | med. | low |
| Anthocyanin color at glume center: | med. | med. |
| Anthocyanin ring at glume base: | present | absent |
| Compactness of tassel: | med. | tight |
| Tassel length, central spike (cm): | 18 | 19 |
| Tassel length, side branches (cm): | 13 | 11 |
| Tassel angle (degree): | 45° | 30° |
| Number of tassel branches: | 6 | 6 |
| Tendency for secondary branching off of side tassel branches. | no | no |
| Uniformity (anther, color, silk, ht.): | uniform | uniform |
| Peduncle length (cm): | 7 | 8 |
| Pollen shed: | med. | med. |
| Anther color: | green | yellow |
| Glume color: | purple & green | purple |
| Silk color: | green | green |
| Fresh husk color: | Lt. green | Lt. green |
| C. LEAVES | | |
| Leaf angle: | semi-erect | very erect |
| Number of leaves below ear: | 8 | 8 |
| Number of leaves above | 6 | 6 |

TABLE 1-continued

4P33339 VARIETY DESCRIPTION INFORMATION

| Type: | 4P33339 dent | B73 dent |
|---|---|---|
| ear: | | |
| Leaf color: | med. | med. |
| Leaf length (cm): | 63 | 69 |
| Leaf width (cm): | 8 | 8 |
| Anthocyanin at leaf blade borders: | low | none |
| Hairiness of leaf edges: | med. | low |
| Hairiness of leaf close to midrib | med. | low |
| Wavy leaf margins: | present | absent |
| Leaf blade wrinkles: | absent | absent |
| D. STALK AND ROOTS | | |
| Plant height to top of tassel (cm): | 190 | 230 |
| Plant length to top ear node (cm): | 68 | 102 |
| Tendency to tiller: | low | low |
| Number of tillers: | none | none |
| Anthocyanin pigment of nodes: | none | none |
| Anthocyanin pigment of internodes: | low | low |
| Hairiness of stalk leaf sheath: | low | low |
| Number of levels of brace root development | 1–2 | 2 |
| Anthocyanin pigment of brace roots: | high | med. |
| E. EAR TRAITS | | |
| Cob color: | red | pink |
| Cob diameter at midpoint (cm): | 2.5 | 3.0 |
| Ear diameter (cm): | 4.0 | 5.0 |
| Ear length (cm): | 17 | 15 |
| Ear shape: | cylind. conical | cylind. |
| Shank length (cm): | 6 | 3 |
| Number of shank internodes: | 3 | 3 |
| Husk length: | longer | longer |
| Husk leaves on husk: | absent | absent |
| Husk leaf length (cm): | 24 | 19 |
| Husk tightness: | loose | med. |
| Husk extension: | 2 = med. | 2 = med. |
| Ear position at dry husk stages: | pendent | pendent |
| Number of kernel rows: | 14 | 18 |
| Straightness of kernel rows: | straight | straight |
| Uniformity (cob color, ear type): | uniform | uniform |
| F. MATURITY | | |
| Days, emergence to 50% silking: | 77 | 78 |
| Days, emergence to 50% pollen shed: | 75 | 77 |
| Days, 50% silk to ½ milk: | 49 | 52 |
| G. KERNEL (DRY) | | |
| Size | | |
| a. length (mm): | 11 | 12 |
| b. width (mm): | 8 | 7.5 |
| c. thick (mm): | 4.0 | 3.0 |
| Shape grade (% round): | 20–40 | <20 |
| Pericarp color: | colorless | colorless |
| Aleurone color: | bronze | varies. |
| Endosperm color: | yellow | yellow |
| Endosperm type: | normal | normal |
| Weight/100 seeds (g): | 26.5 | 22 |
| H. DISEASE RESISTANCE | | |
| Diplodia stalk rot: | susc. | susc. |
| Fusarium stalk rot: | susc. | susc. |
| Gibberella stalk rot: | susc. | susc. |
| Northern leaf blight: | res. | res. |
| Southern leaf blight: | susc. | susc. |
| Southern rust: | susc. | susc. |
| Maize dwarf mosaic: | susc. | susc. |
| I. INSECT RESISTANCE | | |
| Corn borer: | susc. | susc. |
| Earworm: | susc. | susc. |
| Northern corn rootworm: | susc. | susc. |
| Western corn rootworm: | susc. | susc. |
| Southern corn rootworm: | susc. | susc. |

TABLE 2

ELECTROPHORESIS RESULTS ISOZYME GENOTYPES FOR 4P33339

Isozyme data was generated for inbred corn line P33339 according to the procedure described in Stuber, C. W. et al. (1988), "Techniques and scoring procedures for starch gel electrophoresis of enzymes from maize (*Zea mays* L.)," Technical Bulletin 286, March 1988, from North Carolina Agricultural Research Service, North Carolina State University, Raleigh, North Carolina.

Isozyme Profiles

| Isozyme | 4P33339 | B73 |
|---|---|---|
| ACP1 | 4/4 | 2/2 |
| Amp1 | 4/4 | 4/4 |
| Amp3 | 4/4 | 5/5 |
| Glu1 | 7/7 | 7/7 |
| Idh1 | 4/4 | 4/4 |
| Idh2 | 6/6 | 4/4 |
| Mdh1 | 6/6 | 6/6 |
| Mdh2 | 6/6 | 3.5/3.5 |
| Mdh3 | 16/16 | 16/16 |
| Mdh4 | 12/12 | 12/12 |
| Mdh5 | 12/12 | 12/12 |
| Pgd1 | 3.8/3.8 | 3.8/3.8 |
| Pgd2 | 5/5 | 5/5 |
| Pgm1 | 9/9 | 9/9 |
| Pgm2 | 4/4 | 4/4 |

TABLE 3

INBRED YIELD & KERNEL CHARACTERISTICS*

| Inbred | Yield | Kernel % >18.5 | Kernel % 18.5–16.5 | Kernel % <16.5 |
|---|---|---|---|---|
| B73 | 48.0 | 23.0 | 42.0 | 35.0 |
| 4P33339 | 34.0 | 46.5 | 37.5 | 16.0 |

*2 years at 3 locations, 6 replications each

TABLE 4

Hybrid Comparisons

| | Pt Ht | Ear Ht | Pop | Stalk Lodg | Root Lodg | Drop Ear | Emr | Apr | Tst Wt | % MST | YLD | Y/M |
|---|---|---|---|---|---|---|---|---|---|---|---|---|
| 4P33339 Hybrid No. 1 | 100 | 39 | 24.7 | 2.8 | 0.8 | 0.1 | 1.9 | 1.0 | 52.0 | 21.8 | 163.3 | 7.5 |
| Test Hybrid No. 1 | 102 | 42 | 24.7 | 5.4 | 1.4 | 0.3 | 1.7 | 2.0 | 52.5 | 21.0 | 158.1 | 7.5 |
| Locations | (42) | (42) | (58) | (58) | (58) | (58) | (6) | (2) | (4) | (58) | (58) | (58) |
| 4-P33339 Hybrid No. 2 | 98 | 40 | 24.8 | 3.5 | 0.3 | 0.1 | 2.7 | 0.0 | 53.7 | 23.4 | 143.7 | 6.1 |
| Test Hybrid No. 2 | 93 | 38 | 25.4 | 4.8 | 0.8 | 0.1 | 3.7 | 0.0 | 54.6 | 23.1 | 146.4 | 6.3 |
| Locations | (23) | (24) | (28) | (28) | (28) | (28) | (3) | (0) | (3) | (28) | (28) | (28) |
| 4P33339 Hybrid No. 3 | 98 | 47 | 23.9 | 2.9 | 4.8 | 0.2 | 0.0 | 0.0 | 0.0 | 19.3 | 169.0 | 8.8 |
| Test Hybrid No. 3 | 96 | 45 | 24.7 | 2.4 | 3.7 | 0.2 | 0.0 | 0.0 | 0.0 | 19.7 | 164.9 | 8.4 |
| Locations | (6) | (6) | (14) | (14) | (14) | (14) | (0) | (0) | (0) | (14) | (14) | (14) |
| 4P33339 Hybrid No. 1 | 99 | 38 | 24.7 | 1.5 | 0.1 | 0.1 | 0.0 | 1.0 | 0.0 | 21.5 | 166.3 | 7.8 |
| P3733 | 101 | 40 | 25.0 | 1.3 | 0.5 | 0.1 | 0.0 | 1.8 | 0.0 | 20.9 | 162.5 | 7.8 |
| Locations | (27) | 27 | (31) | (31) | (31) | (31) | (0) | (2) | (0) | (31) | (31) | (31) |
| 4P33339 Hybrid No. 4 | 93 | 38 | 24.9 | 3.6 | 0.7 | 0.0 | 2.0 | 1.7 | 55.8 | 21.0 | 162.3 | 7.7 |
| P3733 | 99 | 40 | 25.1 | 3.2 | 0.3 | 0.2 | 3.0 | 1.8 | 58.4 | 21.7 | 165.3 | 7.6 |
| Locations | (39) | (40) | (47) | (47) | (47) | (47) | (1) | (2) | (3) | (47) | (47) | (47) |

What is claimed is:

1. Inbred corn seed designated 4P33339 and having ATCC Deposit No. 97177.

2. A corn plant produced by the seed of claim 1 and its parts.

3. A tissue culture of regenerable cells of the corn plant designated 4P33339 and having ATCC Deposit No. 97177.

4. An $F_1$ hybrid corn plant having 4P33339 as a parent, wherein 4P33339 has ATCC Deposit No. 97177.

5. Corn seed which results from a cross of the corn plant designated 4P33339 with another corn plant that is not 4P33339, wherein 4P33339 has ATCC Deposit No. 97177.

6. A tissue culture of regenerable cells of an $F_1$ hybrid corn plant which is progeny of 4P33339, wherein 4P33339 has ATCC Deposit No. 97177.

7. Corn seed which, when grown under suitable conditions, gives rise to the $F_1$ hybrid corn plant of claim 4.

* * * * *

UNITED STATES PATENT AND TRADEMARK OFFICE
CERTIFICATE OF CORRECTION

PATENT NO. : 5,489,744
DATED : February 6, 1996
INVENTOR(S) : Lyndall W. Dallas

It is certified that error appears in the above-indentified patent and that said Letters Patent is hereby corrected as shown below:

Column 7, Line 65: "varies." should read --varieg.--.

Column 8, Line 31: "P33339" should read --4P33339--.

Column 9, Table 4, Line 12: "4-P33339" should read --4P33339--.

Column 9, Table 4, Ear Ht Column, 12th Row: "(27)  27  (31)  (31)" should read --(27)  (27)  (31)  (31)--.

Signed and Sealed this

Eighteenth Day of June, 1996

*Attest:*

BRUCE LEHMAN

*Attesting Officer*  Commissioner of Patents and Trademarks